(12) United States Patent
Oh et al.

(10) Patent No.: US 11,366,520 B2
(45) Date of Patent: Jun. 21, 2022

(54) METHOD FOR ANALYZING ELEMENT INDUCING MOTION SICKNESS IN VIRTUAL-REALITY CONTENT AND APPARATUS USING THE SAME

(71) Applicant: Electronics and Telecommunications Research Institute, Daejeon (KR)

(72) Inventors: Hee-Seok Oh, Seoul (KR); Seung-Woo Nam, Daejeon (KR); Wook-Ho Son, Daejeon (KR); Beom-Ryeol Lee, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 321 days.

(21) Appl. No.: 16/563,645

(22) Filed: Sep. 6, 2019

(65) Prior Publication Data
US 2020/0183495 A1 Jun. 11, 2020

(30) Foreign Application Priority Data
Dec. 7, 2018 (KR) .................. 10-2018-0157566

(51) Int. Cl.
*G06F 3/01* (2006.01)
*A61B 5/00* (2006.01)
(Continued)

(52) U.S. Cl.
CPC ............ *G06F 3/015* (2013.01); *A61B 5/4076* (2013.01); *G06F 3/013* (2013.01); *G06F 30/20* (2020.01);
(Continued)

(58) Field of Classification Search
None
See application file for complete search history.

(56) References Cited

U.S. PATENT DOCUMENTS

2012/0148146 A1 6/2012 Kim et al.
2014/0176607 A1 6/2014 Yang et al.
(Continued)

FOREIGN PATENT DOCUMENTS

KR 1020120065915 A 6/2012
KR 1020140016061 A 2/2014
(Continued)

OTHER PUBLICATIONS

Yao, Richard, et al. "Oculus vr best practices guide." Oculus VR 4 (2014): 27-35.*
(Continued)

*Primary Examiner* — Ryan M Gray
(74) *Attorney, Agent, or Firm* — William Park & Associates Ltd.

(57) ABSTRACT

Disclosed herein are a method and apparatus for analyzing elements inducing motion sickness in VR content. The method includes acquiring objective data based on an experiment using the VR content for measuring VR motion sickness, the experiment being conducted according to a predetermined protocol; acquiring subjective data input from the multiple participants of the experiment; and constructing a database based on the objective data and the subjective data and analyzing the degree of motion sickness induced by each of the content elements of the VR content using statistical information based on the database.

10 Claims, 7 Drawing Sheets

(51) Int. Cl.
  *G09G 5/00* (2006.01)
  *G06T 19/00* (2011.01)
  *G06F 30/20* (2020.01)

(52) U.S. Cl.
  CPC ......... *G06T 19/006* (2013.01); *G09G 5/003* (2013.01); *G09G 2340/14* (2013.01)

(56) References Cited

U.S. PATENT DOCUMENTS

| | | | |
|---|---|---|---|
| 2018/0096517 A1* | 4/2018 | Mallinson | G02B 27/0093 |
| 2018/0096518 A1* | 4/2018 | Mallinson | A63F 13/53 |
| 2018/0204266 A1* | 7/2018 | King | G06F 16/9535 |
| 2018/0256115 A1* | 9/2018 | Campbell | G16H 50/30 |
| 2018/0260026 A1* | 9/2018 | Drake | G06F 3/016 |
| 2019/0236836 A1* | 8/2019 | Mallinson | G06N 3/04 |
| 2020/0128160 A1* | 4/2020 | Ikei | H04N 5/2257 |
| 2021/0233317 A1* | 7/2021 | Son | G06N 20/00 |

FOREIGN PATENT DOCUMENTS

| | | |
|---|---|---|
| KR | 1020150143087 A | 12/2015 |
| KR | 1020170104846 A | 9/2017 |
| KR | 1020180105879 A | 10/2018 |

OTHER PUBLICATIONS

Kim, Hyun K., et al. "Virtual reality sickness questionnaire (VRSQ): Motion sickness measurement index in a virtual reality environment." Applied ergonomics 69 (2018): 66-73.*

A. Singla et al., "Measuring and comparing QoE and simulator sickness of omnidirectional videos in different head mounted displays," QoMEX, 2017.

H. Olymada et al., "A pilot study on pupillary and cardiovascular changes induced by stereoscopic video movies," J. NeuroEng. Rehabilitation, 2007.

J. L. Dorado et al., "Ramps are better than stairs to reduce cybersickness in applications based on a HMD and a gamepad," IEEE Symp. 3DUI, 2014.

* cited by examiner

METHOD FOR ANALYZING ELEMENT INDUCING MOTION SICKNESS IN VIRTUAL-REALITY CONTENT AND APPARATUS USING THE SAME

CROSS REFERENCE TO RELATED APPLICATION

This application claims the benefit of Korean Patent Application No. 10-2018-0157566, filed Dec. 7, 2018, which is hereby incorporated by reference in its entirety into this application.

BACKGROUND OF THE INVENTION

1. Technical Field

The present invention relates generally to technology for analyzing elements that induce motion sickness in Virtual Reality (VR) content, and more particularly to technology for quantitatively analyzing motion sickness that is caused when viewing VR content.

2. Description of the Related Art

Viewing Virtual Reality (VR) content imposes an experience recognized as being awkward from a biological perspective and causes discordance between visual perception and what is expected from other sensory organs. Such discordance results in VR motion sickness, which has harmful effects on the human body.

In order to prevent VR motion sickness and to produce VR content that feels more natural, it is necessary to correctly detect the causes of VR motion sickness and to refer to information about the quantitative degree of motion sickness induced by various kinds of elements taken into account when the content is produced, for example, camera movement, object movement, special effects, a scenario, and the like.

However, the relationship between VR motion sickness and various types of VR content has been understood with respect to a single element, and thus there is a lack of biopsychological data, experimental results, and reference VR content to which producers or distributors can refer.

Also, experiments related to the causes of VR motion sickness have usually been conducted on a small number of participants, for example, about 20 people. Some of the experiments achieve meaningful results, but not enough is known to construct a database pertaining to VR motion sickness, which includes a lot of elements attracting academic or industrial interest and which is to be used for research and development.

DOCUMENTS OF RELATED ART (Patent Document 1) Korean Patent Application Publication No. 10-2012-0065915, published on Jun. 21, 2012 and titled "Apparatus and method for measuring visual discomfort in stereoscopic image system and recording medium on which program for executing method is recorded".

SUMMARY OF THE INVENTION

An object of the present invention is to collect data pertaining to VR content scenes, which are creatively produced by incorporating elements inducing VR motion sickness therein, through an experiment conducted on a large number of participants according to a logical experimental protocol, thereby constructing a large-scale database related to VR motion sickness.

Another object of the present invention is to store data pertaining to various elements inducing VR motion sickness in a single database, thereby analyzing VR motion sickness in a quantitative manner for various purposes.

In order to accomplish the above objects, a method for analyzing elements inducing motion sickness in Virtual Reality (VR) content according to the present invention includes acquiring objective data based on an experiment using the VR content for measuring VR motion sickness, the experiment being conducted according to a predetermined protocol; acquiring subjective data input from multiple participants of the experiment; and constructing a database based on the objective data and the subjective data and analyzing the degree of motion sickness induced by each of the content elements of the VR content using statistical information based on the database.

Here, the objective data may include at least one of a content parameter corresponding to each of the multiple content elements included in the VR content, an image displayed to the multiple participants during the experiment, bio-signal data measured from the multiple participants, and eye-tracking data measured from the multiple participants.

Here, the subjective data may correspond to values indicative of subjective motion-sickness levels, acquired from the multiple participants.

Here, the objective data and the subjective data may be acquired before and after the experiment is conducted.

Here, the predetermined protocol may include processes of providing consent, filling out a Motion Sickness Susceptibility Questionnaire (MSSQ), filling out a Simulator Sickness Questionnaire (SSQ), measuring a bio-signal, receiving a training session, measuring VR motion sickness, checking a subjective motion-sickness level, filling out an additional SSQ, and taking a rest.

Here, the VR content may be generated based on at least one of the content elements including a background, the complexity of camera movement, camera acceleration, camera speed, a field of view, an independent visual background, content length, and information about whether the VR content is controllable.

Here, measuring the VR motion sickness may be configured to measure the VR motion sickness as many times as the preset number of sessions depending on the content elements.

Here, the bio-signal data may include at least one of an electroencephalogram (EEG), an electrocardiogram (ECG), and a galvanic skin response (GSR).

Here, the eye-tracking data may include at least one of information about the coordinates of an eye gaze on the displayed image, information about the size of a pupil, information about the gradient of the pupil, information about whether the pupil is detected, and information about eye blinks.

Here, analyzing the degree of motion sickness may be configured such that a difference between pieces of objective data, acquired before and after the experiment is conducted, and a difference between pieces of subjective data, acquired before and after the experiment is conducted, are extracted for each of the multiple participants and the degree of motion sickness induced by each of the content elements is analyzed based on the differences.

Also, an apparatus for analyzing elements inducing motion sickness in Virtual Reality (VR) content according to an embodiment of the present invention includes a processor for acquiring objective data based on an experiment, which is conducted according to a predetermined protocol, using the VR content for measuring VR motion sickness, acquiring subjective data input from multiple participants of the experiment, constructing a database based on the objective data and the subjective data, and analyzing the degree of motion sickness induced by each of the content elements of the VR content using statistical information based on the database; and memory for storing at least one of the VR content, the objective data, and the subjective data.

Here, the subjective data may correspond to values indicative of subjective motion-sickness levels, acquired from the multiple participants.

Here, the objective data and the subjective data may be acquired before and after the experiment is conducted.

Here, the predetermined protocol may include processes of providing consent, filling out a Motion Sickness Susceptibility Questionnaire (MSSQ), filling out a Simulator Sickness Questionnaire (SSQ), measuring a bio-signal, receiving a training session, measuring VR motion sickness, checking a subjective motion-sickness level, filling out an additional SSQ, and taking a rest.

Here, the VR content may be generated based on at least one of the content elements including a background, the complexity of camera movement, camera acceleration, camera speed, a field of view, an independent visual background, content length, and information about whether the VR content is controllable.

Here, measuring the VR motion sickness may be configured to measure the VR motion sickness as many times as the preset number of sessions depending on the content elements.

Here, the bio-signal data may include at least one of an electroencephalogram (EEG), an electrocardiogram (ECG), and a galvanic skin response (GSR).

Here, the eye-tracking data may include at least one of information about the coordinates of an eye gaze on the displayed image, information about the size of a pupil, information about the gradient of the pupil, information about whether the pupil is detected, and information about eye blinks.

Here, the processor may extract a difference between pieces of objective data, acquired before and after the experiment is conducted, and a difference between pieces of subjective data, acquired before and after the experiment is conducted, for each of the multiple participants and analyze the degree of motion sickness induced by each of the content elements based on the differences.

Also, a database for analyzing elements inducing motion sickness according to an embodiment of the present invention includes Virtual Reality (VR) content produced for measuring VR motion sickness; a predetermined protocol for an experiment for analyzing elements inducing the VR motion sickness based on the VR content; subjective data input from multiple participants of the experiment; and objective data acquired from the multiple participants based on the experiment.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
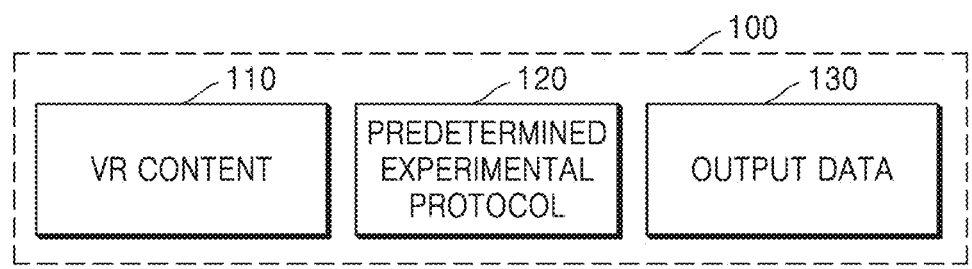
FIG. 1 is a view that shows the configuration of a motion sickness analysis database for analyzing elements inducing motion sickness in VR content according to an embodiment of the present invention.

The present invention will be described in detail below with reference to the accompanying drawings. Repeated descriptions and descriptions of known functions and configurations which have been deemed to unnecessarily obscure the gist of the present invention will be omitted below. The embodiments of the present invention are intended to fully describe the present invention to a person having ordinary knowledge in the art to which the present invention pertains. Accordingly, the shapes, sizes, etc. of components in the drawings may be exaggerated in order to make the description clearer.

Hereinafter, a preferred embodiment of the present invention will be described in detail with reference to the accompanying drawings.

FIG. 1 is a view that shows the configuration of a motion sickness analysis database for analyzing elements inducing motion sickness in VR content according to an embodiment of the present invention.

Referring to FIG. 1, the motion sickness analysis database 100 for analyzing elements inducing motion sickness in VR content according to an embodiment of the present invention may include VR content 110, which is to be used to measure VR motion sickness in order to more effectively analyze the same in a quantitative manner, a predetermined experimental protocol 120, and output data 130 acquired through experimentation.

Here, the VR content 110 is content that is produced in order to measure VR motion sickness, and may be configured with various content scenes in order to measure the degree of motion sickness induced by each content element.

Here, the VR content 110 may be generated based on at least one of content elements including a background, the complexity of camera movement, camera acceleration, camera speed, a field of view, an independent visual background, content length, and information about whether the VR content is controllable. That is, VR content 110 may include different content scenes depending on the content elements.

Here, the predetermined experimental protocol 120 may be design information pertaining to the process of an experiment actually conducted using the VR content 110.

For example, the predetermined experimental protocol 120 according to an embodiment of the present invention may include stages corresponding to providing consent, filling out a Motion Sickness Susceptibility Questionnaire (MSSQ), filling out a Simulator Sickness Questionnaire (SSQ), measuring bio-signals, receiving a training session, measuring VR motion sickness, checking a subjective degree of motion sickness, filling out an additional SSQ, and taking a rest.

Here, the output data 130 may be objective data and subjective data acquired from the participants before and after the experiment is conducted.

Here, the objective data may include at least one of a content parameter corresponding to each of the multiple content elements included in the VR content 110, an image displayed to the multiple participants during the experiment, bio-signal data measured from the multiple participants, and eye-tracking data measured from the multiple participants.

Here, the subjective data may be values indicative of subjective motion-sickness levels, acquired from the multiple participants.

Accordingly, the motion sickness analysis database 100 configured as shown in FIG. 1 may enable an experiment to be conducted using the VR content 110 according to the predetermined experimental protocol 120 and analyze the degree of motion sickness induced by each content element using statistical information based on the output data 130, which is acquired before and after the experiment.

Figure 2:
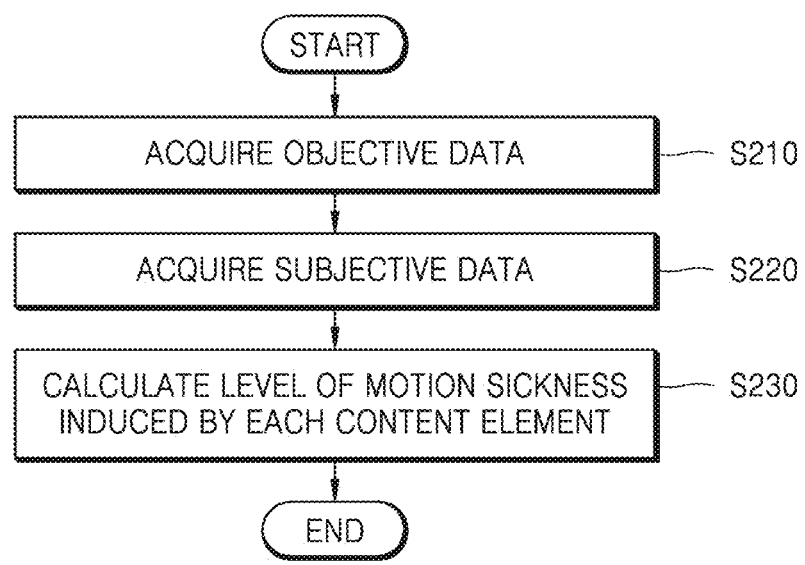
FIG. 2 is a flowchart that shows a method for analyzing elements inducing motion sickness in VR content according to an embodiment of the present invention.

FIG. 2 is a flowchart that shows a method for analyzing elements inducing motion sickness in VR content according to an embodiment of the present invention.

Referring to FIG. 2, in the method for analyzing elements inducing motion sickness in VR content according to an embodiment of the present invention, objective data is acquired at step S210 based on an experiment using VR content for measuring VR motion sickness. Here, the experiment is conducted according to a predetermined protocol.

Here, the VR content may include content scenes produced for measuring VR motion sickness. Here, the content scene may be a continually played section in which elements inducing VR motion sickness are incorporated.

Here, the VR content may be generated based on at least one of content elements including a background, the complexity of camera movement, camera acceleration, camera speed, a field of view, an independent visual background, content length, and information about whether the VR content is controllable.

Figure 3:
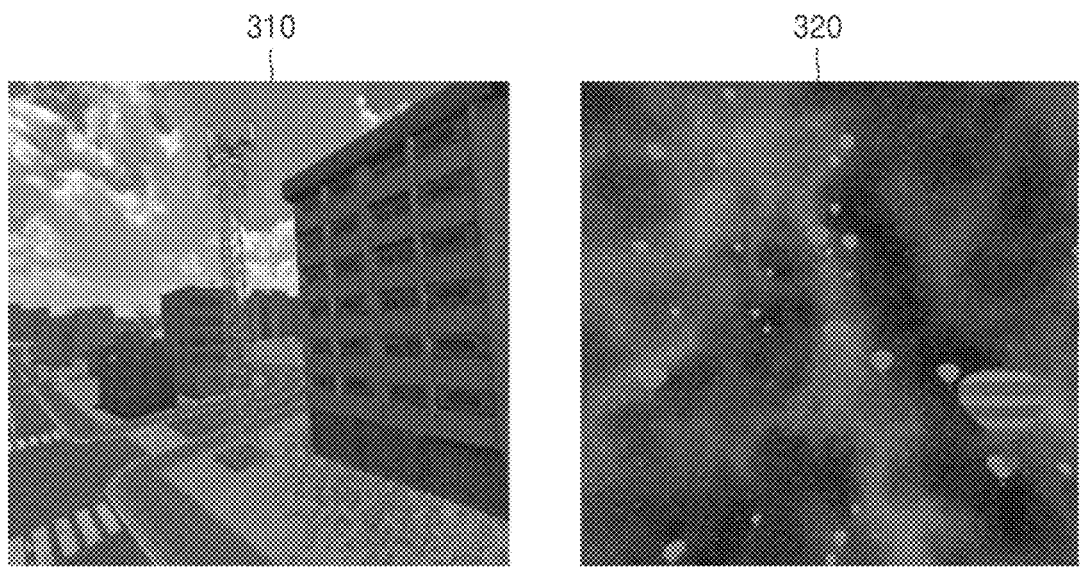
FIGS. 3 to 6 are views that show examples of VR content scenes according to the present invention.

For example, because a background containing a familiar image encountered in daily life suppresses VR motion sickness, the VR content according to the present invention may be produced so as to include a content scene 310 having a background of downtown and a content scene 320 having a background of cosmic space, as shown in FIG. 3.

Here, the two content scenes 310 and 320 illustrated in FIG. 3 may include the following in terms of elements inducing VR motion sickness.

First, because the presence of a floor in VR space helps the viewer of VR content perceive the vertical component of gravity (an element inducing motion sickness in the vestibular system), the influence of presence/absence of a floor on VR motion sickness may be determined.

Also, the degree of VR motion sickness that is induced depending on the brightness of a background may be measured.

Also, because spatial complexity in a content scene is an element inducing VR motion sickness, analysis thereon may be performed by classifying content scenes into two content scenes 310 and 320 depending on the background.

Also, because the presence of a large number of objects in a downtown background decreases the speed of rendering by hardware, the influence of rendering latency on VR motion sickness may be determined.

In another example, a content scene created using the movement and rotation of a complex camera with multi-axis motion control is more likely to induce VR motion sickness than a content scene created using a single camera that simply rotates or moves up and down, back and forth, or to the left and right. Accordingly, the VR content according to the present invention may be produced so as to include a content scene created using the simple camera movement and a content scene created using the complex camera movement.

In another example, in the case of a content scene created using the movement or rotation of a camera, the acceleration visually conveyed to a viewer is associated with the ability to perceive gravity-inertia acceleration in visual/vestibular systems. Accordingly, the VR content according to the present invention may be produced so as to include a content scene including acceleration and a content scene including no acceleration.

In another example, in the case of a content scene created using the movement or rotation of a camera, the absolute velocity visually conveyed to a viewer also affects VR motion sickness. Accordingly, the VR content according to the present invention may be produced so as to include a high-speed content scene and a low-speed content scene.

Figure 4:
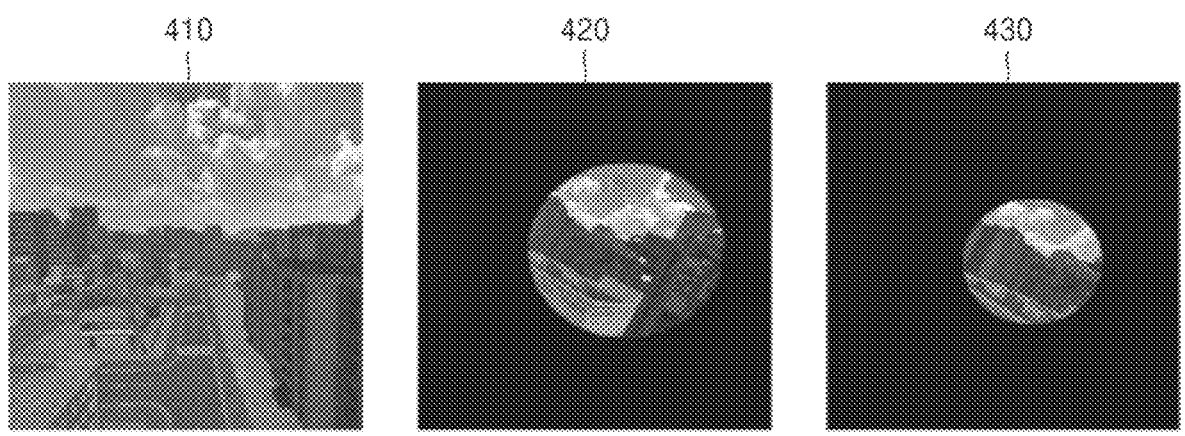

In another example, when a viewer views VR content, a decrease in a field of view may reduce the degree of VR motion sickness. Accordingly, the VR content according to the present invention may be produced so as to include a content scene with a wide field of view 410, a content scene with a medium field of view 420, and a content scene with a narrow field of view 430, as shown in FIG. 4.

Figure 5:
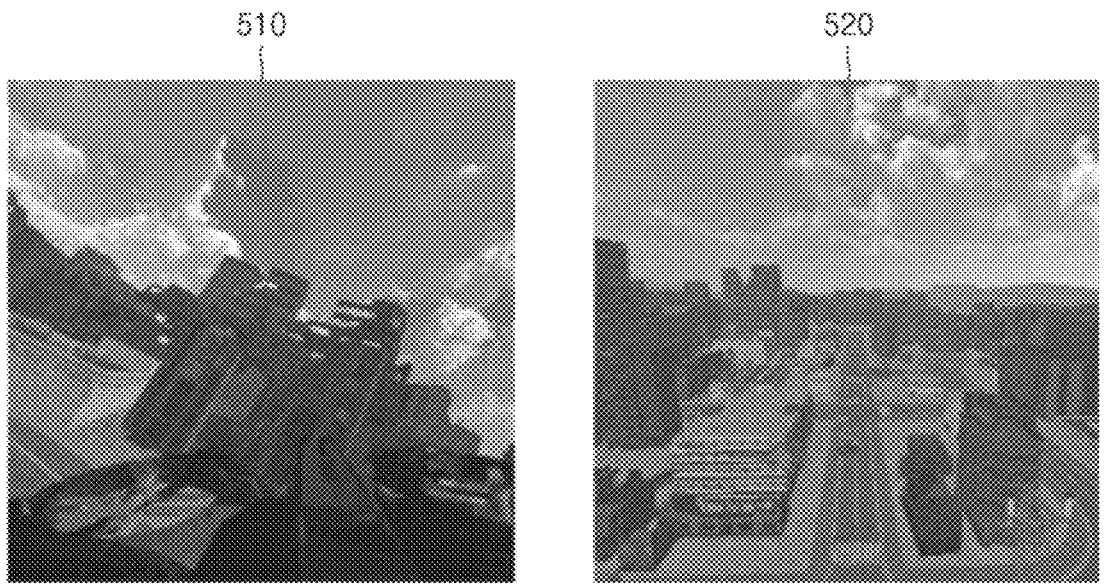

In another example, because a fixed object in a VR content scene may help in suppressing VR motion sickness, the VR content according to the present invention may be produced so as to include a content scene with an independent visual background (IVB) 510 and a scene without an IVB 520, as shown in FIG. 5.

In another example, because the time spent viewing VR content may affect the degree of VR motion sickness experienced by a viewer, the VR content according to the present invention may be produced so as to include a long content scene and a short content scene.

Figure 6:
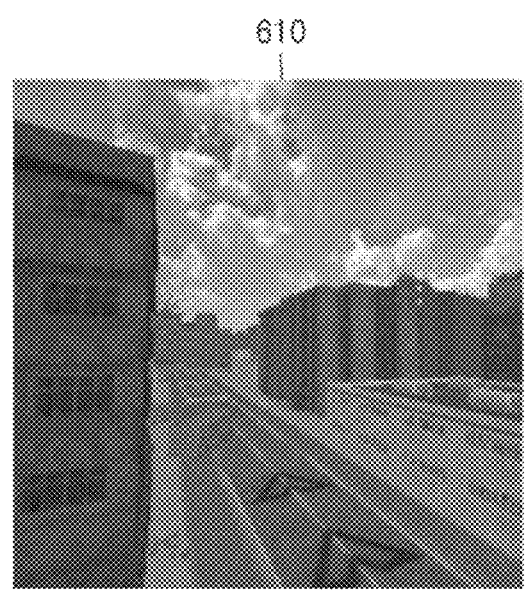

In another example, when VR content is controllable using an external controller, because the viewed image can be changed through control over the motion in the VR content depending on the intention of the viewer, VR motion sickness may be alleviated. Accordingly, the VR content according to the present invention may be produced so as to include a controllable content scene and an uncontrollable content scene. Here, in the case of a controllable content scene, it is necessary to provide guidance for the movement direction in VR space. Accordingly, a direction indicator and information about a destination may be displayed, as shown in the content scene 610 in FIG. 6, as long as they do not interfere with the scene being viewed.

As described above, VR content may be produced so as to include content scenes in which various types of content elements described in the above examples are incorporated, and the list of 52 content scenes according to these examples is as shown in the following Table 1. [Table 1]

TABLE 1

| scene indeX | background | complexity | camera | | | | | | whether control is possible |
|---|---|---|---|---|---|---|---|---|---|
| | | | rotation and movement | acceleration | speed | field of view | IVB | length | |
| S001 | downtown | complex | $(t_f, r_r, r_y)$ | X | normal | wide | X | short | ○ |
| S002 | downtown | complex | $(t_f, r_r, r_y, r_p)$ | X | normal | wide | X | short | ○ |
| S003 | downtown | complex | $(t_f, r_r, r_y, r_p)$ | X | normal | wide | X | short | ○ |
| S004 | downtown | complex | $(t_f, r_r, r_y, r_p)$ | X | normal | wide | X | short | ○ |
| S005 | downtown | complex | $(t_f, r_r, r_y, r_p)$ | X | normal | wide | X | short | ○ |
| S006 | downtown | complex | $(t_f, r_r, r_y, r_p)$ | X | normal | wide | X | short | ○ |
| S007 | downtown | complex | $(t_f, r_r, r_y)$ | X | normal | wide | X | long | ○ |
| S008 | downtown | complex | $(t_f, r_r, r_y)$ | X | normal | wide | X | long | ○ |
| S101 | cosmic space | simple | $r_y$ | X | normal | wide | X | short | X |
| S102 | cosmic space | simple | $r_r$ | X | normal | wide | X | short | X |
| S103 | cosmic space | simple | $r_p$ | X | normal | wide | X | short | X |
| S104 | cosmic space | simple | $t_f$ | X | normal | wide | X | short | X |
| S105 | cosmic space | simple | $t_b$ | X | normal | wide | X | short | X |
| S106 | cosmic space | simple | $t_l$ | X | normal | wide | X | short | X |
| S107 | cosmic space | simple | $t_u$ | X | normal | wide | X | short | X |
| S108 | cosmic space | simple | $t_d$ | X | normal | wide | X | short | X |
| S109 | cosmic space | complex | $(t_f, r_p)$ | X | normal | wide | X | short | X |
| S110 | cosmic space | complex | $(t_f, r_r, r_y)$ | X | normal | wide | X | short | X |
| S111 | cosmic space | complex | $(t_f, r_r, r_y, r_p)$ | X | normal | wide | X | short | X |
| S112 | cosmic space | complex | $(t_f, r_r, r_y)$ | X | fast | wide | X | short | X |
| S113 | cosmic space | complex | $(t_f, r_r, r_y, r_p)$ | X | fast | wide | X | short | X |
| S114 | cosmic space | complex | $(t_f, r_r, r_y)$ | X | normal | medium | X | short | X |
| S115 | cosmic space | complex | $(t_f, r_r, r_y)$ | X | normal | narrow | X | short | X |
| S116 | cosmic space | complex | $(t_f, r_r, r_y)$ | ○ | normal | wide | X | short | X |
| S117 | cosmic space | complex | $(t_f, r_r, r_y, r_p)$ | ○ | normal | wide | X | short | X |
| S118 | cosmic space | complex | $(t_f, r_r, r_y, r_p)$ | ○ | normal | wide | ○ | short | X |
| S201 | downtown | simple | $r_y$ | X | normal | wide | X | short | X |
| S202 | downtown | simple | $r_r$ | X | normal | wide | X | short | X |
| S203 | downtown | simple | $r_p$ | X | normal | wide | X | short | X |
| S204 | downtown | simple | $t_f$ | X | normal | wide | X | short | X |
| S205 | downtown | simple | $t_b$ | X | normal | wide | X | short | X |
| S206 | downtown | simple | $t_l$ | X | normal | wide | X | short | X |
| S207 | downtown | simple | $t_u$ | X | normal | wide | X | short | X |
| S208 | downtown | simple | $t_d$ | X | normal | wide | X | short | X |
| S209 | downtown | complex | $(t_f, r_p)$ | X | normal | wide | X | short | X |
| S210 | downtown | complex | $(t_f, r_r, r_y)$ | X | normal | wide | X | short | X |
| S211 | downtown | complex | $(t_f, r_r, r_y, r_p)$ | X | normal | wide | X | short | X |
| S212 | downtown | complex | $(t_f, r_r, r_y)$ | X | fast | wide | X | short | X |
| S213 | downtown | complex | $(t_f, r_r, r_y, r_p)$ | X | fast | wide | X | short | X |
| S214 | downtown | complex | $(t_f, r_r, r_y)$ | X | normal | medium | X | short | X |
| S215 | downtown | complex | $(t_f, r_r, r_y)$ | X | normal | narrow | X | short | X |
| S216 | downtown | complex | $(t_f, r_r, r_y)$ | ○ | normal | wide | X | short | X |
| S217 | downtown | complex | $(t_f, r_r, r_y, r_p)$ | ○ | normal | wide | X | short | X |
| S218 | downtown | complex | $(t_f, r_r, r_y, r_p)$ | ○ | normal | wide | ○ | short | X |
| S219 | downtown | complex | $(t_f, r_r, r_y)$ | X | normal | wide | X | short | X |
| S220 | downtown | complex | $(t_f, r_r, r_y)$ | X | normal | wide | X | short | X |
| S221 | downtown | complex | $(t_f, r_r, r_y)$ | X | normal | wide | X | short | X |
| S222 | downtown | complex | $(t_f, r_r, r_y)$ | X | normal | wide | X | short | X |
| S223 | downtown | complex | $(t_f, r_r, r_y)$ | X | normal | wide | X | short | X |
| S224 | downtown | complex | $(t_f, r_r, r_y)$ | X | normal | wide | X | long | X |
| S225 | downtown | complex | $(t_f, r_r, r_y)$ | X | normal | wide | X | long | X |
| S226 | downtown | complex | $(t_f, r_r, r_y)$ | ○ | normal | wide | X | long | X |

Figure 7:
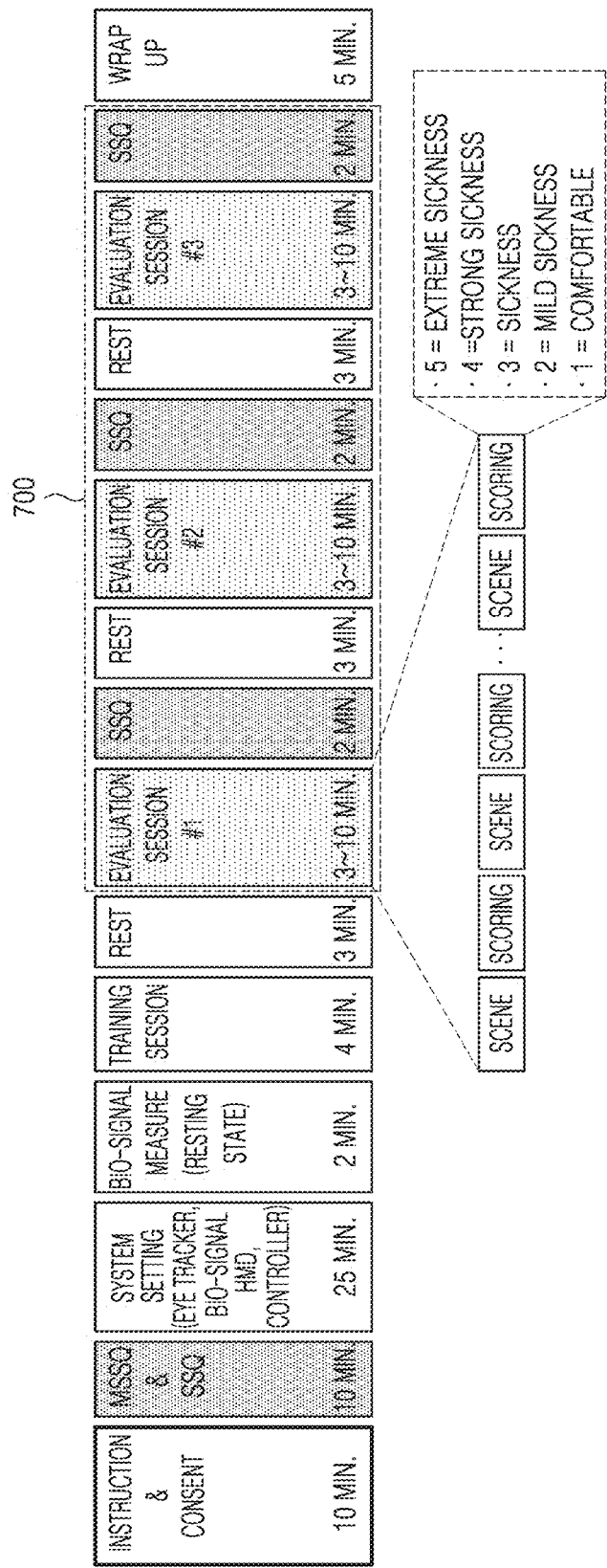
FIG. 7 is a view that shows an example of an experimental protocol according to the present invention.

Here, the present invention designs a predetermined protocol for measuring the degree of VR motion sickness, as shown in FIG. 7, thereby acquiring robust data.

Here, the predetermined protocol may be configured to include providing consent, filling out a Motion Sickness Susceptibility Questionnaire (MSSQ), filling out a Simulator Sickness Questionnaire (SSQ), measuring bio-signals, receiving a training session, measuring VR motion sickness, checking a subjective degree of motion sickness, filling out an additional SSQ, and taking a rest.

Hereinafter, an example of the process of conducting an experiment according to the sequence of stages in the protocol illustrated in FIG. 7 will be described in detail.

First, the experiment according to an embodiment of the present invention may be conducted on middle-aged and older male and female groups after getting permission from the National Bioethics Committee. Here, each group may include fifty or more participants, and the experiment may be conducted on a total of 200 or more participants.

Then, information about the experiment is provided to the participants, and various consent forms signed by the participants may be acquired.

Then, a Motion Sickness Susceptibility Questionnaire (MSSQ) and a Simulator Sickness Questionnaire (SSQ) filled out by each of the participants may be acquired. Here, the MSSQ may be a questionnaire pertaining to the participant's susceptibility to motion sickness based on his or her personal experience, and the SSQ may be a questionnaire pertaining to 16 motion sickness symptoms, each of which is checked with respect to three categories, which are 'nausea', 'oculomotor', and 'disorientation'. Here, the SSQ may be acquired from the participants before and after the experiment is conducted.

Then, before the participants view VR content, their bio-signals in a normal state may be measured and acquired.

Then, a training session is provided to the participants, whereby the participants may practice the entire process of the experiment before the official experiment is started.

Then, after a sufficient break time is allowed, VR content is provided, and the degree of VR motion sickness may be measured.

Here, VR motion sickness may be measured as many times as the preset number of sessions depending on the content elements.

Here, like the VR motion sickness measurement section 700 illustrated in FIG. 7, VR motion sickness may be measured over multiple sessions classified based on the content element to be analyzed. For example, as shown in FIG. 7, three sessions may be configured such that 8 controllable content scenes having a background of downtown are output in the first session, 18 uncontrollable content scenes having a background of cosmic space are output in the second session, and 26 uncontrollable content scenes having a background of downtown are output in the third session.

Here, after the participants view the content scenes of each session, the degrees of VR motion sickness experienced by the participants may be checked. For example, the degree of VR motion sickness may be checked as five levels, corresponding to comfort, slight motion sickness, moderate motion sickness, strong motion sickness, and severe motion sickness.

Figure 8:
FIG. 8 is a view that shows an example of a survey screen for a Simulator Sickness Questionnaire (SSQ) according to the present invention.

Also, after the participants view the content scenes of each session, an SSQ implemented in the form of a Graphical User Interface (GUI) as shown in FIG. 8 is additionally provided to the participants, and a result may be acquired therefrom. That is, when three sessions are provided as shown in FIG. 7, the three SSQ results may be acquired.

Here, the objective data may include at least one of a content parameter corresponding to each of the multiple content elements included in the VR content, an image displayed to the multiple participants during the experiment, bio-signal data measured from the multiple participants, and eye-tracking data measured from the multiple participants.

For example, the content parameters may be parameter data recorded while all of the participants are participating in the experiment by viewing the VR content. That is, the x, y and z coordinates of a camera when it moves, the speed of the camera in x, y and z directions when it moves, the acceleration of the camera in x, y and z directions when it moves, the x, y and z coordinates of the camera when it rotates, the speed of the camera when it rotates around x, y and z axes, the acceleration of the camera when it rotates around x, y and z axes, the x, y and z coordinates of the head of a participant when it moves, the speed of the head of the participant in x, y and z directions when it moves, the acceleration of the head of the participant in x, y and z directions when it moves, the x, y and z coordinates of the head of the participant when it rotates, the speed of the head of the participant when it rotates around x, y and z axes, the acceleration of the head of the participant when it rotates around x, y and z axes, information about control performed by the participant using an external controller, the content scene rendering speed, and the like may be recorded as the content parameters.

In another example, the images displayed to the multiple participants during the experiment are the images actually viewed by each of the participants, and the images may be recorded and provided as video. Here, the recorded video may include a depth map, which includes depth information pertaining to 2D RGB rendering images viewed by the participant or depth information pertaining to rendering images viewed by the participant.

Here, the bio-signal data may include at least one of an electroencephalogram (EEG), an electrocardiogram (ECG), and a galvanic skin response (GSR).

Figure 9:
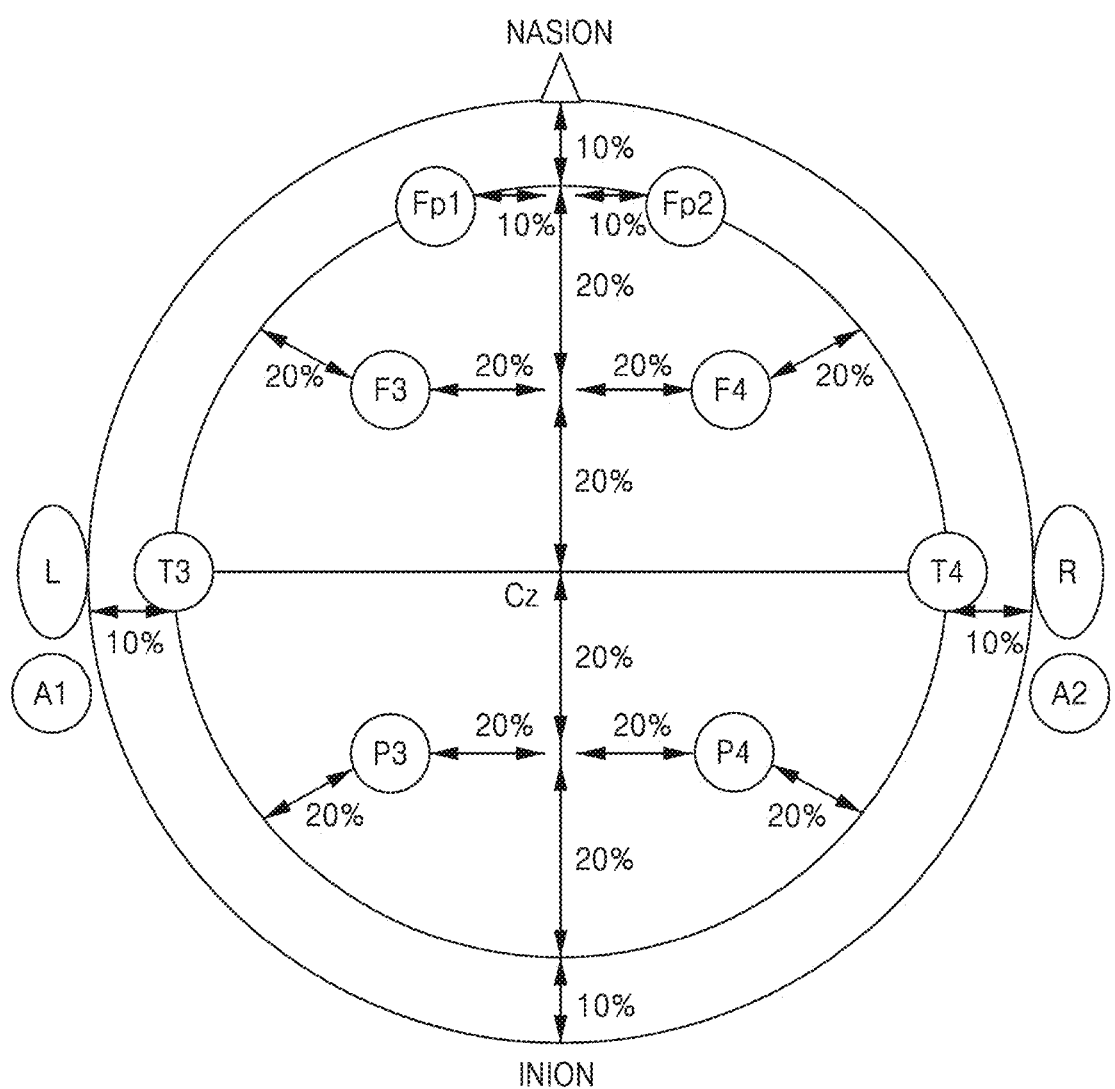
FIG. 9 is a view that shows an example of spots where Electroencephalography (EEG) electrodes are attached in order to collect bio-signal data according to the present invention.

For example, the EEG may be acquired so as to correspond to a change in 8-channel EEG signals measured from spots at which EEG electrodes are attached, as shown in FIG. 9. Here, information about the change in the 8-channel EEG signals may be acquired based on the EEGs measured before and after the experiment is conducted.

In another example, the ECG may be acquired so as to correspond to a change in a single-channel ECG signal, and the change in the single-channel ECG signal may be acquired based on the ECGs measured before and after the experiment is conducted.

In another example, the GSR may be acquired so as to correspond to a change in a single-channel GSR signal, and the change in the single-channel GSR signal may be acquired based on the GSRs measured before and after the experiment is conducted.

Here, the eye-tracking data may include at least one the coordinates of an eye gaze on the image being viewed, the size of a pupil, the gradient of the pupil, information about whether the pupil is detected, and information about eye blinks.

For example, the eye-tracking data may be acquired using an eye tracker installed in a head-mounted display. That is, the x and y coordinates of an eye gaze on the image being viewed, the size of a pupil on an x-y plane, the gradient of the pupil, information about whether the pupil is detected, eye blinks, and the like may be tracked using the eye tracker and acquired as the eye-tracking data.

Also, in the method for analyzing elements inducing motion sickness in VR content according to an embodiment of the present invention, subjective data input from the multiple participants of the experiment is acquired at step S220.

Here, the subjective data may be values indicative of subjective motion-sickness levels acquired from the multiple participants.

For example, the values indicative of subjective motion-sickness levels may be detected based on the results of the MSSQs and SSQs filled out by the participants in the course of the experiment. That is, the degree of motion sickness for each VR content scene may be analyzed using each participant's susceptibility to motion sickness and the result of comparison of the degree of motion sickness in a normal state with the degree of motion sickness measured after the experiment is conducted. Here, scores for 16 motion sickness symptoms in the SSQ may be calculated and used in order to analyze the degree of motion sickness.

Also, in the method for analyzing elements inducing motion sickness in VR content according to an embodiment of the present invention, a database is constructed based on the objective data and the subjective data, and the degree of motion sickness induced by each of the content elements of the VR content is analyzed using statistical information based on the database at step S230.

Here, the objective data and the subjective data may be acquired before and after the experiment is conducted.

Here, the difference between the objective data acquired before the experiment and that acquired after the experiment and the difference between the subjective data acquired before the experiment and that acquired after the experiment are extracted for each of the participants, and the degree of motion sickness induced by each of the content elements of the VR content may be determined based on the differences.

For example, the result of SSQs filled out by the participants before they view the VR content is compared with the result of SSQs filled out by the participants after they view the VR content, whereby quantitative comparison may be performed for 16 motion sickness symptoms and categories such as 'nausea', 'oculomotor', and 'disorientation'.

In another example, bio-signal data measured from the participants before they view the VR content is compared with that measured after they view the VR content, and variation therebetween is monitored, whereby the VR motion sickness may be analyzed.

In another example, the number of eye blinks counted before the participants view the VR content is compared with that counted after they view the VR content, whereby eye strain may be analyzed in a quantitative manner.

Here, the VR motion sickness may be analyzed using the data of each session of the experiment.

For example, when 8 controllable content scenes having a background of downtown are output in the first session, 18 uncontrollable content scenes having a background of cosmic space are output in the second session, and 26 uncontrollable content scenes having a background of downtown are output in the third session, as described in the above example, the results of the SSQs in the first session and those in the second session are compared with each other, whereby the assumption that the controllable VR content induces a lower degree of motion sickness may be evaluated.

Here, using the subjective data and the objective data acquired from each of the content scenes shown in Table 1, the degree of motion sickness induced by the content elements may be analyzed.

For example, when the subjective data and the objective data of the scenes S101 and S102 in Table 1 are analyzed, it may be determined which camera movement, among rolling and pitching, has a greater influence on VR motion sickness.

In another example, when the subjective data and the objective data of the scenes S115 and S116 in Table 1 are analyzed, the influence of a field of view on VR motion sickness may be quantitatively analyzed.

In another example, when the subjective data and the objective data of the scenes S223 and S224 in Table 1 are analyzed, the influence of the time spent viewing VR content on VR motion sickness may be quantitatively analyzed.

Here, the 2D images of the VR space actually viewed by the viewer are provided as video and stored in the database, whereby VR motion sickness for virtual 3D space may be analyzed offline.

Also, modeling based on machine learning may be performed using the data stored in the database according to an embodiment of the present invention, whereby the degree of VR motion sickness induced by arbitrary VR content may be predicted.

Also, although not illustrated in FIG. 2, in the method for analyzing elements inducing motion sickness in VR content according to an embodiment of the present invention, various kinds of information generated during the above-described process of analyzing elements inducing motion sickness in VR content may be stored in a separate storage module.

Through the above-described method for analyzing elements inducing motion sickness in VR content, data pertaining to VR content scenes, creatively produced by incorporating elements inducing VR motion sickness therein, is collected through an experiment conducted on a large number of participants according to a logical experimental protocol, whereby a large-scale database related to VR motion sickness may be constructed.

Also, data pertaining to various elements inducing VR motion sickness is stored in a single database, whereby VR motion sickness may be analyzed in a quantitative manner for various purposes.

Figure 10:
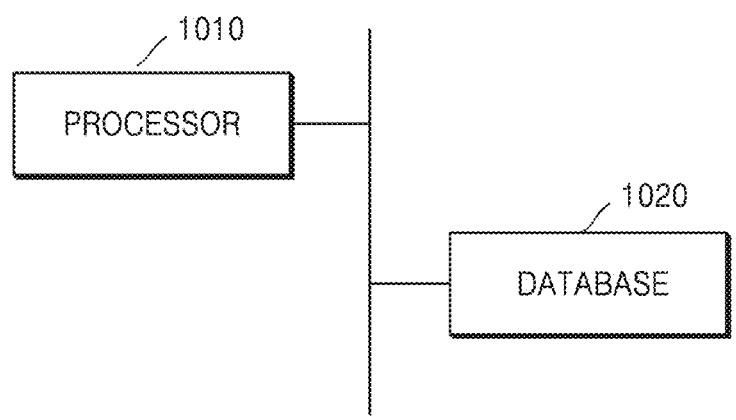
FIG. 10 is a block diagram that shows an apparatus for analyzing elements inducing motion sickness in VR content according to an embodiment of the present invention.

FIG. 10 is a block diagram that shows an apparatus for analyzing elements inducing motion sickness in VR content according to an embodiment of the present invention.

Referring to FIG. 10, the apparatus for analyzing elements inducing motion sickness in VR content according to an embodiment of the present invention includes a processor 1010 and memory 1020.

The processor 1010 acquires objective data based on an experiment using VR content for measuring VR motion sickness, the experiment being conducted according to a predetermined protocol.

Here, the VR content may include content scenes produced for measuring VR motion sickness. Here, the content scene may be a continually played section in which elements inducing VR motion sickness are incorporated.

Here, the VR content may be generated based on at least one of content elements including a background, the complexity of camera movement, camera acceleration, camera speed, a field of view, an independent visual background, content length, and information about whether the VR content is controllable.

For example, because a background containing a familiar image encountered in daily life suppresses VR motion sickness, the VR content according to the present invention may be produced so as to include a content scene 310 having a background of downtown and a content scene 320 having a background of cosmic space, as shown in FIG. 3.

Here, the two content scenes 310 and 320 illustrated in FIG. 3 may include the following, in terms of elements inducing VR motion sickness.

First, because the presence of a floor in VR space helps the viewer of VR content perceive the vertical component of gravity (an element inducing motion sickness in the vestibular system), the influence of presence/absence of a floor on VR motion sickness may be determined.

Also, the degree of VR motion sickness that is induced depending on the brightness of a background may be measured.

Also, because spatial complexity in a content scene is an element inducing VR motion sickness, analysis thereon may be performed by classifying content scenes into two content scenes 310 and 320 depending on the background.

Also, because the presence of a large number of objects in a downtown background decreases the speed of rendering by hardware, the influence of rendering latency on VR motion sickness may be determined.

In another example, a content scene created using the movement and rotation of a complex camera with multi-axis motion control is more likely to induce VR motion sickness than a content scene created using a single camera that simply rotates or moves up and down, back and forth, or to the left and right. Accordingly, the VR content according to the present invention may be produced so as to include a content scene created using the simple camera movement and a content scene created using the complex camera movement.

In another example, in the case of a content scene created using the movement or rotation of a camera, the acceleration visually conveyed to a viewer is associated with the ability to perceive gravity-inertia acceleration in visual/vestibular systems. Accordingly, the VR content according to the present invention may be produced so as to include a content scene including acceleration and a content scene including no acceleration.

In another example, in the case of a content scene created using the movement or rotation of a camera, the absolute velocity visually conveyed to a viewer also affects VR motion sickness. Accordingly, the VR content according to the present invention may be produced so as to include a high-speed content scene and a low-speed content scene.

In another example, when viewing VR content, a decrease in a field of view may reduce the degree of VR motion sickness. Accordingly, the VR content according to the present invention may be produced so as to include a content scene with a wide field of view 410, a content scene with a medium field of view 420, and a content scene with a narrow field of view 430, as shown in FIG. 4.

In another example, because a fixed object in a VR content scene may help in suppressing VR motion sickness, the VR content according to the present invention may be produced so as to include a content scene with an independent visual background (IVB) 510 and a content scene without an IVB 520, as shown in FIG. 5.

In another example, because the time spent viewing VR content may affect the degree of VR motion sickness experienced by a viewer, the VR content according to the present invention may be produced so as to include a short content scene and a long content scene.

In another example, when VR content can be controlled using an external controller, because the viewed image can be changed through control over the motion in the VR content depending on the intention of the viewer, VR motion sickness may be alleviated. Accordingly, the VR content according to the present invention may be produced so as to include a controllable content scene and an uncontrollable content scene. Here, in the case of a controllable content scene, it is necessary to provide guidance for the movement direction in VR space. Accordingly, a direction indicator and information about a destination may be displayed, as shown in the content scene 610 in FIG. 6, as long as they do not interfere with the scene being viewed.

As described above, VR content may be produced so as to include content scenes in which various types of content elements described in the above examples are individually incorporated, and the list of 52 content scenes according to these examples is as shown in the above Table 1.

In the present invention, a predetermined protocol for measuring the degree of VR motion sickness may be designed, as shown in FIG. 7, whereby robust data may be acquired.

Here, the predetermined protocol may be configured to include providing consent, filling out a Motion Sickness Susceptibility Questionnaire (MSSQ), filling out a Simulator Sickness Questionnaire (SSQ), measuring bio-signals, receiving a training session, measuring VR motion sickness, checking a subjective degree of motion sickness, filling out an additional SSQ, and taking a rest.

Hereinafter, an example of the process of conducting an experiment according to the sequence of stages in the protocol illustrated in FIG. 7 will be described in detail.

First, the experiment according to an embodiment of the present invention may be conducted on middle-aged and older male and female groups after getting permission from the National Bioethics Committee. Here, each group may include fifty or more participants, and the experiment may be conducted on a total of 200 or more participants.

Then, information about the experiment is provided to the participants, and various consent forms signed by the participants may be acquired.

Then, a Motion Sickness Susceptibility Questionnaire (MSSQ) and a Simulator Sickness Questionnaire (SSQ) filled out by each of the participants may be acquired therefrom. Here, the MSSQ may be a questionnaire pertaining to the participant's susceptibility to motion sickness based on his or her personal experience, and the SSQ may be a questionnaire pertaining to 16 motion sickness symptoms, each of which is checked with regard to three categories, which are 'nausea', 'oculomotor', and 'disorientation'. Here, the SSQ may be acquired from the participants before and after the experiment is conducted.

Then, before the participants view VR content, their bio-signals in a normal state may be measured and acquired.

Then, a training session is provided to the participants, whereby the participants may practice the entire process of the experiment before the official experiment is started.

Then, after a sufficient break time is allowed, VR content is provided, and the degree of VR motion sickness may be measured.

Here, VR motion sickness may be measured as many times as the preset number of sessions depending on the content elements.

Here, like the VR motion sickness measurement section 700 illustrated in FIG. 7, VR motion sickness may be measured over multiple sessions classified based on the content element to be analyzed. For example, as shown in FIG. 7, three sessions may be configured such that 8 controllable content scenes having a background of downtown are output in the first session, 18 uncontrollable content scenes having a background of cosmic space are output in the second session, and 26 uncontrollable content scenes having a background of downtown are output in the third session.

Here, after the participants view the content scenes of each session, the degree of VR motion sickness experienced by the participants may be checked. For example, the degree of VR motion sickness may be checked as five levels, corresponding to comfort, slight motion sickness, moderate motion sickness, strong motion sickness, and severe motion sickness.

Also, after the participants view the content scenes of each session, an SSQ implemented in the form of a Graphical User Interface (GUI) as shown in FIG. 8 is additionally provided to the participants, and a result may be acquired therefrom. That is, when three sessions are provided as shown in FIG. 7, the three SSQ results may be acquired.

Here, the objective data may include at least one of a content parameter corresponding to each of the multiple content elements included in the VR content, an image displayed to the multiple participants during the experiment, bio-signal data measured from the multiple participants, and eye-tracking data measured from the multiple participants.

For example, the content parameters may be parameter data recorded while all of the participants are participating in the experiment by viewing the VR content. That is, the x, y and z coordinates of a camera when it moves, the speed of the camera in x, y and z directions when it moves, the acceleration of the camera in x, y and z directions when it moves, the x, y and z coordinates of the camera when it rotates, the speed of the camera when it rotates around x, y and z axes, the acceleration of the camera when it rotates around x, y and z axes, the x, y and z coordinates of the head of a participant when it moves, the speed of the head of the participant in x, y and z directions when it moves, the acceleration of the head of the participant in x, y and z directions when it moves, the x, y and z coordinates of the head of the participant when it rotates, the speed of the head of the participant when it rotates around x, y and z axes, the acceleration of the head of the participant when it rotates around x, y and z axes, information about control performed by the participant using an external controller, the content scene rendering speed, and the like may be recorded as the content parameters.

In another example, the images displayed to the multiple participants during the experiment are the images actually viewed by each of the participants, and the images may be recorded and provided as video. Here, the recorded video may include a depth map, which includes depth information pertaining to 2D RGB rendering images viewed by the participant or depth information pertaining to rendering images viewed by the participant.

Here, the bio-signal data may include at least one of an electroencephalogram (EEG), an electrocardiogram (ECG), and a galvanic skin response (GSR).

For example, the EEG may be acquired so as to correspond to as a change in 8-channel EEG signals measured from spots at which EEG electrodes are attached, as shown in FIG. 9. Here, information about the change in the 8-channel EEG signals may be acquired based on the EEGs measured before and after the experiment is conducted.

In another example, the ECG may be acquired so as to correspond to a change in a single-channel ECG signal, and the change in the single-channel ECG signal may be acquired based on the ECGs measured before and after the experiment is conducted.

In another example, the GSR may be acquired so as to correspond to a change in a single-channel GSR signal, and the change in the single-channel GSR signal may be acquired based on the GSRs measured before and after the experiment is conducted.

Here, the eye-tracking data may include at least one the coordinates of an eye gaze on the image being viewed, the size of a pupil, the gradient of the pupil, information about whether the pupil is detected, and information about eye blinks.

For example, the eye-tracking data may be acquired using an eye tracker installed in a head-mounted display. That is, the x and y coordinates of an eye gaze on the image being viewed, the size of a pupil in an x-y plane, the gradient of the pupil, information about whether the pupil is detected, eye blinks, and the like may be tracked using the eye tracker and acquired as the eye-tracking data.

Also, the processor 1010 acquires subjective data input from the multiple participants of the experiment.

Here, the subjective data may be values indicative of subjective motion-sickness levels acquired from the multiple participants.

For example, the values indicative of subjective motion-sickness levels may be detected based on the results of the MSSQs and SSQs filled out by the participants in the course of the experiment. That is, the degree of motion sickness for each VR content scene may be analyzed using each participant's susceptibility to motion sickness and the result of comparison of the degree of motion sickness in a normal state with the degree of motion sickness measured after the experiment is conducted. Here, scores for 16 motion sickness symptoms in the SSQ may be calculated and used in order to analyze the degree of motion sickness.

Also, the processor 1010 constructs a database based on the objective data and the subjective data and analyzes the degree of motion sickness induced by each of the content elements of VR content using statistical information based on the database.

Here, the objective data and the subjective data may be acquired before and after the experiment is conducted.

Here, the difference between the objective data acquired before the experiment and that acquired after the experiment and the difference between the subjective data acquired before the experiment and that acquired after the experiment are extracted for each of the participants, and the degree of motion sickness induced by each of the content elements of the VR content may be determined based on the differences.

For example, the result of SSQs filled out by the participants before they view the VR content is compared with the result of SSQs filled out by the participants after they view the VR content, whereby quantitative comparison may be performed for 16 motion sickness symptoms and categories such as 'nausea', 'oculomotor', and 'disorientation'.

In another example, bio-signal data measured from the participants before they view the VR content is compared with bio-signal data measured after they view the VR content, and variation therebetween is monitored, whereby the VR motion sickness may be analyzed.

In another example, the number of eye blinks counted before the participants view the VR content is compared with that counted after they view the VR content, whereby eye strain may be analyzed in a quantitative manner.

Here, the VR motion sickness may be analyzed using the data of each session of the experiment.

For example, when 8 controllable content scenes having a background of downtown are output in the first session, 18 uncontrollable content scenes having a background of cosmic space are output in the second session, and 26 uncontrollable content scenes having a background of downtown are output in the third session, as described in the above example, the results of the SSQs in the first session and those in the second session are compared with each other, whereby the assumption that the controllable VR content induces a lower degree of motion sickness may be evaluated.

Here, using the subjective data and the objective data acquired from each of the content scenes shown in Table 1, the degree of motion sickness induced by the content elements may be analyzed.

For example, when the subjective data and the objective data of the scenes S101 and S102 in Table 1 are analyzed, it may be determined which camera movement, among rolling and pitching, has a greater influence on VR motion sickness.

In another example, when the subjective data and the objective data of the scenes S115 and S116 in Table 1 are analyzed, the influence of a field of view on VR motion sickness may be quantitatively analyzed.

In another example, when the subjective data and the objective data of the scenes S223 and S224 in Table 1 are analyzed, the influence of the time spent viewing VR content on VR motion sickness may be quantitatively analyzed.

Here, the 2D images of the VR space actually viewed by the viewer are provided as video and stored in the database, whereby VR motion sickness for virtual 3D space may be analyzed offline.

Also, modeling based on machine learning may be performed using the data stored in the database according to an embodiment of the present invention, whereby the degree of VR motion sickness induced by arbitrary VR content may be predicted.

The memory 1020 stores at least one of VR content, objective data, and subjective data.

Also, the memory 1020 stores various kinds of information generated in the above-described apparatus for analyzing elements inducing motion sickness in VR content according to an embodiment of the present invention.

According to an embodiment, the memory 1020 may be separate from the apparatus for analyzing elements inducing motion sickness in VR content, thereby supporting a function for analyzing elements inducing motion sickness in VR content. Here, the memory 1020 may function as separate mass storage, and may include a control function for performing operations.

Meanwhile, the apparatus for analyzing elements inducing motion sickness in VR content may include memory installed therein, thereby storing information in the apparatus. In an embodiment, the memory is a computer-readable recording medium. In an embodiment, the memory may be a volatile memory unit, and in another embodiment, the memory may be a nonvolatile memory unit. In an embodiment, the storage device is a computer-readable recording medium. In different embodiments, the storage device may include, for example, a hard-disk device, an optical disk device, or any other kind of mass storage.

Using the above-described apparatus for analyzing elements inducing motion sickness in VR content, data pertaining to VR content scenes, creatively produced by incorporating elements inducing VR motion sickness therein, is collected through an experiment that is conducted on a large number of participants according to a logical experimental protocol, whereby a large-scale database related to VR motion sickness may be constructed.

Also, data pertaining to various elements inducing VR motion sickness is stored in a single database, whereby VR motion sickness may be analyzed in a quantitative manner for various purposes.

According to the present invention, data pertaining to VR content scenes, creatively produced by incorporating elements inducing VR motion sickness therein, is collected through an experiment conducted on a large number of participants according to a logical experimental protocol, whereby a large-scale database related to VR motion sickness may be constructed.

Also, the present invention may store data pertaining to various elements inducing VR motion sickness in a single database, thereby analyzing VR motion sickness in a quantitative manner for various purposes.

Also, the present invention provides images viewed by users as video, whereby the correlation between VR motion sickness and information about the images that a viewer actually views in virtual 3D space may be determined.

Also, the present invention provides a guideline on producing VR content and quantitative criteria, thereby facilitating rating of various types of VR content (such as games, movies, educational content, and the like).

Also, the present invention may provide an international standard reference related to the production and use of VR content.

As described above, the method and apparatus for analyzing elements inducing motion sickness in VR content according to the present invention are not limitedly applied to the configurations and operations of the above-described embodiments, but all or some of the embodiments may be selectively combined and configured, so that the embodiments may be modified in various ways.

What is claimed is:

1. A method for analyzing elements inducing motion sickness in Virtual Reality (VR) content, comprising:

acquiring objective data based on an experiment using the VR content for measuring VR motion sickness, the experiment being conducted according to a predetermined protocol;

acquiring subjective data input from multiple participants of the experiment; and constructing a database based on the objective data and the subjective data and analyzing a degree of motion sickness induced by each of content elements of the VR content using statistical information based on the database, wherein the VR content includes different content scenes depending on value of the content elements; and wherein the content elements of the VR content include a camera movement, a camera acceleration, a camera speed, and a object movement.

2. The method of claim 1, wherein the objective data includes at least one of bio-signal data measured from the multiple participants, and eye-tracking data measured from the multiple participants.

3. The method of claim 1, wherein the subjective data corresponds to values indicative of subjective motion-sickness levels, acquired from the multiple participants.

4. The method of claim 1, wherein the objective data and the subjective data are acquired before and after the experiment is conducted.

5. The method of claim 1, wherein the predetermined protocol includes processes of providing consent, filling out a Motion Sickness Susceptibility Questionnaire (MSSQ), filling out a Simulator Sickness Questionnaire (SSQ) corresponding to each content scene, measuring a bio-signal, and taking a rest.

6. The method of claim 2, wherein the bio-signal data includes at least one of an electroencephalogram (EEG), an electrocardiogram (ECG), and a galvanic skin response (GSR).

7. An apparatus for analyzing elements inducing motion sickness in Virtual Reality (VR) content, comprising:

a processor for acquiring objective data based on an experiment, which is conducted according to a predetermined protocol, using the VR content for measuring VR motion sickness, acquiring subjective data input from multiple participants of the experiment, constructing a database based on the objective data and the subjective data, and analyzing a degree of motion sickness induced by each of content elements of the VR content using statistical information based on the database; and memory for storing at least one of the VR content, the objective data, and the subjective data, wherein the VR content includes different content scenes depending on value of the content elements; and wherein the content elements of the VR content include a background, a complexity of camera movement, a camera acceleration, a camera speed, a field of view, an independent visual background, a content length, and controllability.

8. The apparatus of claim 7, wherein the objective data includes at least one of a content parameter corresponding to each of the content elements included in the VR content, an image displayed to the multiple participants during the experiment, bio-signal data measured from the multiple participants, and eye-tracking data measured from the multiple participants.

9. The apparatus of claim 7, wherein the predetermined protocol includes processes of providing consent, filling out a Motion Sickness Susceptibility Questionnaire (MSSQ), filling out a Simulator Sickness Questionnaire (SSQ) corresponding to each content scene, measuring a bio-signal, and taking a rest.

10. The apparatus of claim 8, wherein the bio-signal data includes at least one of an electroencephalogram (EEG), an electrocardiogram (ECG), and a galvanic skin response (GSR).

* * * * *